United States Patent [19]

Emmett et al.

[11] Patent Number: 4,962,110

[45] Date of Patent: Oct. 9, 1990

[54] PYRIDAZINONE DERIVATIVES

[75] Inventors: John C. Emmett, Welwyn; William J. Coates, Welwyn Garden City, both of England

[73] Assignee: Smith Kline & French Laboratories Limited, Welwyn Garden City, England

[21] Appl. No.: 392,687

[22] Filed: Aug. 10, 1989

Related U.S. Application Data

[63] Continuation of Ser. No. 837,975, Mar. 10, 1986, abandoned.

[51] Int. Cl.$^5$ .................... C07D 401/10; A61K 31/50
[52] U.S. Cl. ...................................... 514/252; 544/238
[58] Field of Search ................ 514/252; 544/238, 239, 544/241

[56] References Cited

U.S. PATENT DOCUMENTS

| | | | |
|---|---|---|---|
| 4,521,415 | 6/1985 | Katakami et al. | 544/238 |
| 4,661,484 | 4/1987 | Okushima et al. | 514/242 |
| 4,734,415 | 3/1988 | Sircar et al. | 514/247 |
| 4,904,664 | 2/1990 | Brain et al. | 544/238 |
| 4,906,628 | 3/1990 | Coates | 544/238 |

Primary Examiner—Nicholas S. Rizzo
Attorney, Agent, or Firm—William T. King; Stuart R. Suter; Edward T. Lentz

[57] ABSTRACT

The invention relates to 2-aminopyrimidinone derivatives that have utility as cardiac stimulants. A compound of the invention is 6-[4-(1,4-dihydro-4-oxo-2-pyrimidinylamino)phenyl]-5-methyl-4,5-dihydro-3(2H)-pyridazinone.

21 Claims, No Drawings

PYRIDAZINONE DERIVATIVES

This is a continuation of application Ser. No. 837,975, filed Mar. 10, 1986.

The present invention relates to 2-aminopyrimidinone derivatives and in particular to such compounds having a phenyl dihydropyridazinone substituent. This invention further relates to pharmaceutical compositions containing them and a method of stimulating cardiac activity by administering them. The compounds of this invention are phosphodiesterase type III inhibitors and are of use in combatting such conditions wherein such inhibition is thought to be beneficial. Thus the compounds of this invention are positive inotropic agents and vasodilators and are therefore of value in combatting cardiovascular disease, in particular congestive heart failure. In addition the compounds of this invention inhibit platelet aggregation and therefore have an antithrombotic effect. Furthermore the compounds of this invention are bronchodilators and are therefore of use in combatting chronic obstructive lung diseases such as asthma and bronchitis. The major utility of the compounds of this invention is in the treatment of congestive heart failure, for such treatment the compounds have a very desirable profile of activity.

Congestive heart failure is traditionally treated with cardiac glycosides, for example digoxin and digitoxin, and sympathomimetic agents. The glycosides have pronounced toxic effects with a low therapeutic index. The sympathomimetic agents generally do not have the desired profile of activity and are not orally effective. Amrinone is a marketed compound of interest that is reported to be an inotropic agent. This has an undesirable profile of side-effects when administered orally and development is being restricted to other modes of administration. Clearly there is a continuing need for orally active inotropic agents that have a good therapeutic profile.

Accordingly the present invention provides compounds of the formula (I):

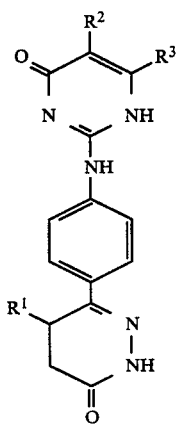
(I)

and pharmaceutically acceptable salts thereof, wherein
$R^1$ is hydrogen or methyl; and
$R^2$ and $R^3$ are independently hydrogen, $C_{1-4}$alkyl, phenyl($C_{1-4}$)alkyl or pyridyl($C_{1-4}$)alkyl, any of such groups being optionally substituted by one or two hydroxy, $C_{1-4}$alkoxy or $C_{1-4}$alkyl groups; or $R^2$ and $R^3$ together with the carbon atoms to which they are joined form a benzene ring which is optionally substituted by $C_{1-4}$alkyl.

Suitably $R^1$ is hydrogen. Preferably $R^1$ is methyl.

Suitably $R^2$ is phenyl($C_{1-4}$)alkyl optionally substituted by one or two groups selected from hydroxy, $C_{1-4}$alkoxy and $C_{1-4}$alkyl, for example benzyl, phenethyl, hydroxybenzyl, methoxybenzyl and hydroxyphenethyl. Suitably $R^2$ is pyridyl($C_{1-4}$)alkyl optionally substituted on a ring carbon atom by one or two groups selected from hydroxy, $C_{1-4}$alkoxy and $C_{1-4}$alkyl, for example pyridylmethyl, hydroxypyridylmethyl, methoxypyridylmethyl and methylpyridylmethyl.

More suitably $R^2$ is hydrogen or $C_{1-4}$alkyl optionally substituted by hydroxy or $C_{1-4}$alkoxy, for example methyl, ethyl, n-propyl, n-butyl, hydroxymethyl, hydroxyethyl, methoxymethyl or methoxyethyl.

Preferably $R^2$ is hydrogen or methyl.

Suitably $R^3$ is phenyl($C_{1-4}$)alkyl optionally substituted by one or two groups selected from hydroxy, $C_{1-4}$alkoxy and $C_{1-4}$alkyl, for example benzyl, phenethyl, hydroxybenzyl, methoxybenzyl and hydroxyphenethyl. Suitably $R^3$ is pyridyl($C_{1-4}$)alkyl optionally substituted on a ring carbon atom by one or two groups selected from hydroxy, $C_{1-4}$alkoxy and $C_{1-4}$alkyl, for example pyridylmethyl, hydroxypyridylmethyl, methoxypyridylmethyl and methylpyridylmethyl.

More suitably $R^3$ is hydrogen or $C_{1-4}$alkyl optionally substituted by hydroxy or $C_{1-4}$alkoxy, for example methyl, ethyl, n-propyl, n-butyl, hydroxymethyl, hydroxyethyl, methoxymethyl or methoxyethyl.

Preferably $R^3$ is hydrogen or methyl.

In an alternative $R^2$ and $R^3$ together with the carbon atom to which they are joined form a benzene ring which is optionally substituted by $C_{1-4}$alkyl for example methyl.

Favourably $R^2$ and $R^3$ are both selected from hydrogen or $C_{1-4}$alkyl, in particular one of $R^2$ and $R^3$ is hydrogen or methyl and the other is hydrogen.

Particular compounds of this invention are:
6-[4-(1,4-dihydro-4-oxo-2-pyrimidinylamino)phenyl]-5-methyl-4,5-dihydro-3(2H)-pyridazinone;
6-[4-(1,4-dihydro-6-methyl-4-oxo-2-pyrimidinylamino)-phenyl]-5-methyl-4,5-dihydro-3(2H)-pyridazinone;
6-[4-(1,4-dihydro-5-methyl-4-oxo-2-pyrimidinylamino)-phenyl]5-methyl-4,5-dihydro-3(2H)-pyridazinone; and
6-[4-(1,4-dihydro-4-oxo-2-quinazolinylamino)phenyl]-5-methyl-4,5-dihydro-3(2H)-pyridazinone.

The compounds of the invention are depicted as dihydropyridazin-3(2H)-ones, but of course the present invention covers all tautomeric forms thereof, for example the dihydropyridazinol form and all the tautomeric forms of the aminopyrimidin-4-one group for example the 4-hydroxypyrimidine tautomer, aminopyrimidin-6-one and the 6-hydroxypyrimidine tautomer, and:

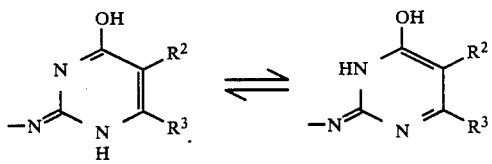

Furthermore the present invention covers all the optical isomeric forms of the compounds of the formula (I) in the racemic and separated forms. In particular when $R^1$ is methyl the (R) isomers of the compounds of the formula (I) (vide infra) are preferred.

Compounds of the formula (I) may form pharmaceutically acceptable salts with metal ions, such as alkali metals for example sodium and potassium, or alkaline earth metals for example calcium and magnesium. The compounds of the formula (I) can also form pharmaceutically acceptable acid addition salts, suitable salts include those formed with hydrochloric, hydrobromic, sulphuric, phosphoric, acetic, citric, maleic, lactic, ascorbic, fumaric, oxalic, methanesulphonic and ethanesulphonic acids.

In order to use a compound of the formula (I) or a pharmaceutically acceptable salt thereof for the treatment of humans and other mammals it is normally formulated in accordance with standard pharmaceutical practice as a pharmaceutical composition.

Compounds of formula (I) and their pharmaceutically acceptable salts may be administered in standard manner for the treatment of the indicated diseases, for example orally, parenterally, trans-dermally, rectally, via inhalation or via buccal administration.

Compounds of formula (I) and their pharmaceutically acceptable salts which are active when given orally or via buccal administration can be formulated as syrups, tablets, capsules and lozenges. A syrup formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include magnesium stearate, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

A typical suppository formulation comprises a compound of formula (I) or a pharmaceutically acceptable salt thereof which is active when administered in this way, with a binding and/or lubricating agent, for example polymeric glycols, gelatins, cocoa-butter or other low melting vegetable waxes or fats.

Typical transdermal formulations comprise of a conventional aqueous or non-aqueous vehicle, for example a cream, ointment, lotion or paste or in the form of a medicated plaster, patch or membrane.

Typical compositions for inhalation are in the form of a solution, suspension or emulsion that may be administered in the form of an aerosol using a conventional propellant such as dichlorodifluoromethane or trichlorofluoromethane.

Preferably the composition is in unit dosage form, for example a tablet, capsule or metered aerosol dose, so that the patient may administer to himself a single dose.

Each dosage unit for oral administration contains suitably from 0.01 mg/Kg to 3 mg/Kg, and preferably from 0.05 mg/Kg to 1.5 mg/Kg, and each dosage unit for parenteral administration contains suitably from 0.001 mg/Kg to 1 mg/Kg, of a compound of formula (I) or a pharmaceutically acceptable salt thereof calculated as the free base.

The daily dosage regimen for oral administration is suitably about 0.01 mg/Kg to 12 mg/Kg, of a compound of formula (I) or a pharmaceutically acceptable salt thereof calculated as the free base. The daily dosage regimen for parenteral administration is suitably about 0.001 mg/Kg to 4 mg/Kg, for example about 0.01 mg/Kg to 1 mg/Kg, of a compound of the formula (I) or a pharmaceutically acceptable salt thereof calculated as the free base. The active ingredient may be administered from 1 to 4 times a day, sufficient to increase cardiac output. The compositions of the present invention have positive inotropic activity and vasodilator activity and are of use in the treatment of cardiovascular diseases which can be treated by compounds having either or both of these activities. One such disease condition is congestive heart failure. The compounds of the invention are also bronchodilators and are useful in chronic obstructive lung disease for example asthma and bronchitis. Such conditions can be treated by administration orally, rectally, parenterally or by inhalation. For administration by inhalation dosages are controlled by a valve, are administered as required and for an adult are conveniently in the range 0.1–5.0 mg of a compound of the formula (I) or a pharmaceutically acceptable salt thereof.

The compounds of this invention may be co-administered with other pharmaceutically active compounds, for example in combination, concurrently or sequentially. Conveniently the compounds of this invention and the other active compound or compounds are formulated in a in combination, concurrently or sequentially. Conveniently the compounds of this invention and the other active compound or compounds are formulated in a pharmaceutical composition. Examples of compounds which may be included in pharmaceutical compositions with the compounds of the formula (I) are vasodilators for example hydralazine, angiotensin converting enzyme inhibitors for example captopril, anti-anginal agents for example isosorbide nitrate, glyceryl trinitrate and pentaerythritol tetranitrate, anti-arrhythmic agents for example quinidine, procainamide and lignocaine, cardioglycosides for example digoxin and digitoxin, calcium antagonists for example verapamil and nifedipine, diuretics such as thiazides and related compounds for example bendrofluazide, chlorothiazide, chlorothalidone, hydrochlorothiazide, and other diuretics for example frusemide and triamterene, and sedatives for example nitrazepam, flurazepam and diazepam.

The compounds of the formula (I) or pharmaceutically acceptable salts thereof may be prepared by a process which comprises:

(a) reacting a compound of the formula (II) with a compound of the formula (III):

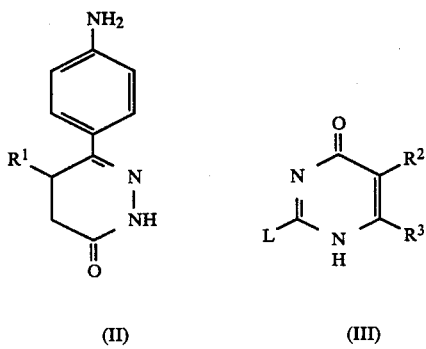

(II)   (III)

(b) reacting a compound of the formula (IV):

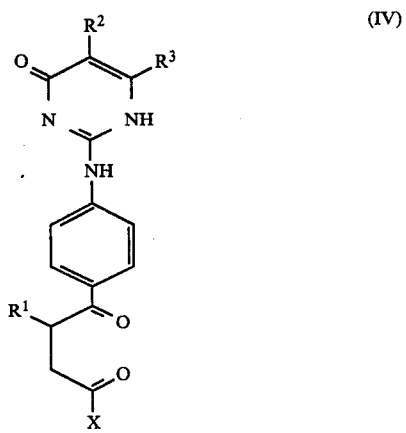

wherein $R^1$, $R^2$ and $R^3$ are as hereinbefore defined, and X is a displaceable group, with hydrazine or a chemical equivalent thereof: and thereafter optionally forming a pharmaceutically acceptable salt.

Suitably in the compounds of the formula (III) L is nitroamino, $C_{1-6}$alkylthio, benzylthio, chloro or bromo. Of these methylthio is preferred.

The reaction of a compound of the formula (II) and a compound of the formula (III) can be performed, at an elevated temperature, in the absence of solvent or in the presence of a substantially inert polar solvent. Conveniently the reaction is performed in a solvent such as $C_{1-6}$alkanol, pyridine or anisole under conditions of reflux.

The compounds of the formula (II) are known from U.S. Pat. No. 3,746,712 and U.S. Pat. No 3,475,431. The compounds of the formula (III) are known or preparable in conventional manner.

The (R) and (S) isomers (respectively the (−) and (+) isomers) of the compound of the formula (II) wherein $R^1$ is methyl can be separated by passage of racemic compound over a chiral phase chromatography column. The appropriate fractions are collected, rechromatographed as necessary, solvent is evaporated and the desired isomer isolated in conventional manner.

The resolved form of a compound of the formula (I) can be prepared by reaction of the corresponding resolved form of a compound of formula (II) with a compound of the formula (III).

The reaction between a compound of the formula (IV) and hydrazine or a chemical equivalent thereof is suitably performed at ambient or elevated temperature, for example 15° C.–120° C., preferably about 30° C.–80° C. or at reflux temperature of a suitable solvent. The reaction is conveniently performed in a solvent such as a $C_{1-4}$alkanol for example methanol, ethanol or n-propanol, or aqueous or glacial acetic acid. Suitably in the compounds of the formula (IV) X is hydroxy, $C_{1-6}$alkoxy, amino or $C_{1-6}$alkylamino.

By a chemical equivalent of hydrazine we mean hydrazine hydrate, hydrazine ethanolate or a similar solvate. Preferably hydrazine is used in the form of hydrazine hydrate.

The compounds of the formula (IV) can be prepared by reacting a compound of the formula (V):

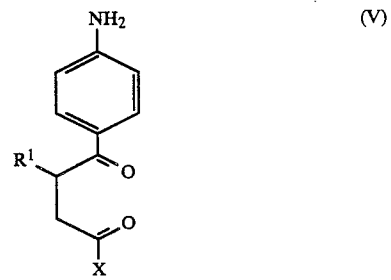

wherein $R^1$ and X are as hereinbefore defined with a compound of the formula (III) as hereinbefore defined; in an analogous manner to that described for reacting compounds of the formulae (II) and (III). The compounds of the formula (V) are known or preparable in conventional manner, see for example the above identified U.S. Patents and Curran et al., J. Med. Chem., 17, p 273 (1974).

Pharmaceutically acceptable acid addition salts of the compounds of the formula (I) may be prepared from the corresponding base of the compounds of the formula (I) in conventional manner. For example the base may be reacted with an acid in a $C_{1-4}$alkanol, or an ion-exchange resin may be used. The salts of the compounds of the formula (I) may be interconverted using ion-exchange resins. Non-pharmaceutically acceptable salts are therefore of use as they can be converted to pharmaceutically acceptable salts.

Pharmaceutically acceptable base addition salts of the compounds of the formula (I) may be prepared by standard methods, for example by reacting a solution of the compound of the formula (I) with a solution of the base.

The following biological test methods, data, description and Examples serve to illustrate this invention.

CARDIAC STIMULANT ACTIVITY—IN VITRO

The compounds of formula (I) and their pharmaceutically acceptable salts are tested for cardiac stimulant activity following a procedure based on that of S. C. Verma and J. H. McNeill (J. Pharm & Exp. Therapeutics, 200, 352–362 (1977)). Guinea pigs (500–700 g) of either sex are sacrificed and the hearts are quickly removed and transferred to a dissecting dish containing oxygenated bathing fluid. While in the bathing medium, the right ventricle is cut into two strips. The strips are each suspended in a 50 ml bath containing Krebs Henseleit solution at 37° C., and the bath is bubbled with 95% oxygen and 5% carbon dioxide. The ventricular strips are electrically stimulated at a frequency of 1.0 Hz, at double the threshold voltage. A resting tension of 1.0 g is applied to the strips and the tension is kept constant by readjustment during an equilibration period of 60 minutes. The bathing fluid is frequently changed during this period. When a steady base line is obtained, a compound under test is added to the bathing fluid and a cumulative concentration response curve is plotted. The compounds for use in the present invention which were tested gave a 50% ($EC_{50}$) increase in the force of contraction of the ventricular strips at concentrations in the bathing fluid of less than $10^{-4}$ molar, thus showing that they have activity as positive inotropic agents.

In the above test method the compound of Example 1 gave an $EC_{50}$ value of $0.6 \times 10^{-6}$ M. In comparison amrinone gave a value of $15 \times 10^{-6}$ M.

CARDIAC STIMULANT ACTIVITY—IN VIVO (ANAESTHETISED CATS)

In anaesthetised cats pretreated with a ganglion blocker (pempidine) and propranolol, the compounds of the Examples caused sustained increases in left ventricular dp/dt max (this is an index of left ventricular contractility) when administered intravenously. The dose to increase left ventricular dp/dt max by 50% is given as the $ED_{50}$.

| Compound of Example | $ED_{50}$ (micromol/kg) | Relative # Duration |
|---|---|---|
| 1 | 0.06 | *** |
| 3 | 3.03 | * |
| 4 | 0.41 | * |
| Amrinone | 5.6 | * |

Relative duration was estimated in the anaesthetised cats following the i.v. administration:
***long
*short

INHIBITION OF PHOSPHODIESTERASES

Three peaks of cyclic nucleotide phosphodiesterase activity [PDE (Peak I), PDE (Peak II) and PDE (Peak III)] from cat heart were separated by chromatography on DEAE-Sepharose CL-6B (Diethylaminoethyl Cellulose with a bead size of 45–165 microns). Sepharose is a registered trademark of Pharmacia Fine Chemicals Inc. The high-speed supernatant from a cat heart homogenate (2 g tissue in 20 ml 20 mM PIPES (Piperazine-N-N'-bis[2-ethanesulfonic acid]), 50 mM Na acetate, pH 6.5) was applied to a $15 \times 1.5$ cm column of DEAE-Sepharose equilibrated with the homogenisation buffer. The PDE activities were eluted with a gradient of 0.05–1 M Na acetate in 20 mM PIPES. There were three major peaks which had the following characteristics:

| PDE (Peak I) - eluted at 0.15 M Na acetate | | | |
|---|---|---|---|
| Substrate | 50 μg/ml calmodulin (+ = added) | Km (μM) | Relative $V_{max}$ |
| cyclic AMP | − | 0.5 | 1 |
| cyclic GMP | − | 1.8 | 1.1 |
| cyclic AMP | + | 0.7 | 6.3 |
| cyclic GMP | + | 1.4 | 7.2 |

| PDE (Peak II) - eluted at 0.3 M Na acetate | | |
|---|---|---|
| Substrate | Km(μM) | Relative $V_{max}$ |
| cyclic AMP | 6 | 1 |
| cyclic GMP | 28 | 0.2 |

| PDE (Peak III) - eluted at 0.5 M Na acetate | | |
|---|---|---|
| Substrate | Km (μM) | Relative $V_{max}$ |
| cyclic AMP | 0.6 | 1 |
| cyclic GMP | 2.9 | 0.4 |

PDE (Peak I) has high affinity for cyclic AMP and cyclic GMP and is characterised by an activation by $Ca^{2+}$/calmodulin complex.

PDE (Peak II) demonstrates relatively low affinities for both cyclic AMP and cyclic GMP and is not affected by $Ca^{2+}$/calmodulin complex.

PDE (Peak III) has high affinity for cyclic AMP. It can also hydrolyse cyclic GMP though the preferred substrate is cyclic AMP. This activity is also insensitive to $Ca^{2+}$/calmodulin activation.

Enzyme assay

The enzyme was assayed by incubation at 37° for 4–30 min in 50 mM Tris, 5 mM $MgCl_2$, pH 7.5 with [3-H] cyclic nucleotide ($4 \times 10^5$ disintegrations $min^{-1}$) and [14-C] nucleotide 5' monophosphate ($3–10^3$ disintegrations $min^{-1}$). The assay was stopped by boiling, and the [3-H] 5'monophosphate product separated from substrate on boronate columns (Davis, C. W. and Daly, J. W. (1979) J. Cyclic Nucleotide Res., 5, 65–74). The reaction mixture was diluted with 0.5 ml 100 mM HEPES (N-2-Hydroxyethylpiperazine-N'-2-ethanesulfonic acid), 100 mM NaCl, pH 8.5, and applied to the column. The column was extensively washed with the same buffer, and the 5' nucleotide eluted with 6 ml 0.25 M acetic acid. The recovery of product as judged by [14-C] recovery was approximately 80%. All assays were linear with time of incubation and concentration of enzyme over the range used in these experiments.

CALCULATION OF $IC_{50}$ VALUES $IC_{50}$ values (the concentration of inhibitor required for 50% inhibition of activity) were obtained for PDE (Peak III) by incubation of the enzyme at 1 μM cyclic AMP, and a range of inhibitor concentrations from $0.1 \times IC_{50}$ to $100 \times IC_{50}$.

| Compound of Example | $IC_{50} \times 10^{-6}M$ |
|---|---|
| 1 | 0.69 |
| 2 | 0.45 |
| 3 | 1.12 |
| 4 | 0.15 |
| Amrinone | 51.8 |
| Milrinone | 2.2 |

DESCRIPTION 1

(+) and (−)-6-(4-Aminophenyl)-5-methyl-4,5-dihydro-3(2H)-pyridazinone

Racemic 6-(4-aminophenyl)-5-methyl-4,5-dihydro-3(2H)-pyridazinone (2.0 g) dissolved in a mixture of acetonitrile (80 ml) and dichloromethane (30 ml) was added to a column of ionically bound (R)-N-(3,5-dinitrobenzoylphenyl)glycine on 40 μm γ-aminopropyl silanized silica (2.1 kg), packed at 1104 kPa (160 p.s.i.) (by slurrying with dichloromethane (1.5 L)) in a Jobin-Yvon medium pressure liquid chromatography system. The column was eluted with dichloromethane/methanol (199:1) over 9 hours at a rate of 80 ml $min^{-1}$. Detection was by u.v. at 280 nm. A broad peak was obtained from which fractions were collected. The earlier fractions were enriched (−) enantiomer. These fractions were combined and re-chromatographed through the same column with the same eluant.

The selected column fractions were evaporated, triturated with diethyl ether, filtered and the resultant solid washed with diethyl ether and dried at 80° C. for 18 hours to give (−)-6-(4-aminophenyl)-5-methyl-4,5-dihydro-3(2H)-pyridazinone, in approximately 100% enantiomeric excess, m.p. 203°–4° C.; $[\alpha]25/D = -399°$ [concentration 0.74% in ethanol:water:conc. HCl (17:2:1)].

A sample of the (−) isomer was reacted with 3-bromopropionyl chloride to afford enantiomerically pure (−)-6-[4-(3-bromopropionamido)phenyl]-5-methyl-4,5-dihydro-3(2H)-pyridazinone, the absolute configuration of which was shown by a X-ray diffraction study to be (R).

The later fractions from the first column were enriched (+) enantiomer (approximately 75% enrichment) which was subjected to medium pressure liquid chromatography (Jobin-Yvon system) over a column of ionically bound (S)-N-(3,5-dinitrobenzoyl)phenylglycine on 25–40 μm γ-aminopropyl silanized silica (55 g) eluting with dichloromethane/methanol (199:1). The appropriate fractions were combined with fractions from another run and re-chromatographed through the same column.

The selected column fractions were evaporated, triturated with diethyl ether, filtered and the resultant solid washed with diethyl ether and dried at 80° C. for 18 hours to give (+)-6-(4-aminophenyl)-5-methyl-4,5-dihydro-3(2H)-pyridazinone, in approximately 100% enantiomeric excess, m.p. 206°–8° C.; $[\alpha]25/D = +376°$ [concentration 0.74% in ethanol:water:conc. HCl (17:2:1)].

EXAMPLE 1

6-[4-(1,4-Dihydro-4-oxo-2-pyrimidinylamino)phenyl]-5-methyl-4,5-dihydro-3(2H)-pyridazinone A stirred mixture of 6-(4-aminophenyl)-5-methyl-4,5-dihydro-3(2H)-pyridazinone (2.6 g) and 2-methylthiouracil (2.73 g) in dry pyridine (40 ml) was heated under reflux for 26 hours. The mixture was evaporated under reduced pressure and the residue was triturated with water, filtered to remove unreacted 2-methylthiouracil and allowed to stand to deposit the product (1.78 g). A second crop (2.4 g) was obtained by evaporation of the filtrate and trituration of the residue with ether-ethanol. The crude combined product was purified by column chromatography (silica gel, 10:1 chloroform:methanol) to give the pure title compound (1.2 g) m.p. 268°–270° C. (recrystallised from 50% aqueous ethanol).

EXAMPLE 2

6-[4-(1,4-Dihydro-6-methyl-4-oxo-2-pyrimidinylamino)phenyl]-5-methyl-4,5-dihydro-3(2H)-pyridazinone A stirred mixture of 6-(4-aminophenyl)-5-methyl-4,5-dihydro-3(2H)-pyridazinone (2.6 g) and 6-methyl-2-methylthiopyrimidin-4-one (3 g) in dry pyridine (40 ml) was heated under reflux for 72 hours. The volume was reduced by evaporation and the crude product (3.16 g) was collected and washed with ethanol. Recrystallisation twice from dimethylformamide gave the title compound (1.39 g), m.p. 314°–318° C. (dec).

EXAMPLE 3

6-[4-(1,4-Dihydro-5-methyl-4-oxo-2-pyrimidinylamino)-phenyl]-5-methyl-4,5-dihydro-3(2H)-pyridazinone A stirred mixture of 6-(4-aminophenyl)-5-methyl-4,5-dihydro-3(2H)-pyridazinone (3.25 g) and 5-methylthiouracil (2.5 g) was heated at 180° C. for 1½ hours. The residual gum was dissolved in hot aqueous ethanol and the solution was evaporated. Trituration of the residue with chloroform:methanol (10:1) gave the crude product as a solid (0.78 g), m.p. 260°–270° C. The filtrate was evaporated and the residue was heated at 180° C. for one hour. Purification of the residue by column chromatography (silica gel, chloroform:methanol, 25:1) gave a further amount of product (0.73 g).

Recrystallisation from aqueous ethanol of the products from two reactions gave the title compound, m.p. 270°–275° C., in 57% recovery.

EXAMPLE 4

6-[4-(1,4-Dihydro-4-oxo-2-quinazolinylamino)phenyl]-5-methyl-4,5-dihydro-3(2H)-pyridazinone A stirred mixture of 6-(4-aminophenyl)-5-methyl-4,5-dihydro-3(2H)-pyridazinone (2 g) and 2-methylthio-4-quinazolinone (2.98 g) in dry pyridine (15 ml) was heated under reflux for 90 hours. The mixture was filtered and the solid digested with boiling acetonitrile to leave a solid (0.66 g), m.p. 313°–319° C. The combined filtrates were evaporated and the residue was heated with pyridine (3 ml) in the absence of a condenser, in an oil bath at 160° C. for 3 hours. The residue was digested with acetonitrile as before to give the title compound, (0.55 g), m.p. 312°–315° C.

The products from two reactions were recrystallised together from aqueous dimethylformamide to give the title compound, m.p. 313°–316° C., in 64% recovery.

EXAMPLE 5

(R)-6-[4-(1,4-Dihydro-4-oxo-2-pyrimidinylamino)-phenyl]-5-methyl-4,5-dihydro-3(2H)-pyridazinone A stirred mixture of (R)-6-(4-aminophenyl)-5-methyl-4,5-dihydro-3(2H)-pyridazinone and 2-methylthiouracil in dry pyridine are heated together to afford the title compound.

EXAMPLE 6

Ethyl 3-[4-(1,4-dihydro-4-oxo-2-pyrimidinylamino)-benzoyl]butyrate

A stirred mixture of ethyl 3-(4-aminobenzoyl)butyrate and 2-methylthiouracil in dry pyridine are heated together to afford the title compound.

EXAMPLE 7

Pharmaceutical compositions for oral administration are prepared by combining the following:

|  | % w/w | | |
| --- | --- | --- | --- |
| 6-[4-(1,4-dihydro-4-oxo-2-pyrimidinylamino)phenyl]-5-methyl-4,5-dihydro-3(2H)-pyridazinone, | 0.5 | 3.0 | 7.14 |
| 2% w/w Soya lecithin in soya bean oil | 90.45 | 88.2 | 84.41 |
| Hydrogenated vegetable shortening and beeswax | 9.05 | 8.8 | 8.45 |

The formulations are then filled into individual soft gelatin capsules.

What is claimed is:

1. A compound of the formula (I):

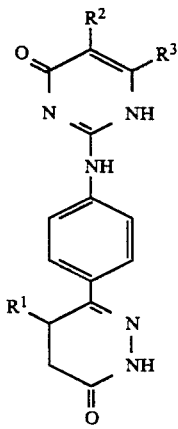

or a pharmaceutically acceptable salt thereof, wherein
$R^1$ is hydrogen or methyl; and
$R^2$ and $R^3$ are independently hydrogen, $C_{1-4}$alkyl, phenyl($C_{1-4}$)alkyl or pyridyl($C_{1-4}$)alkyl, any of such groups being optionally substituted by one or two hydroxy, $C_{1-4}$alkoxy or $C_{1-4}$alkyl groups; or $R^2$ and $R^3$ together with the carbon atoms to which they are joined form a benzene ring which is optionally substituted by $C_{1-4}$alkyl.

2. A compound according to claim 1 wherein $R^1$ is methyl.

3. A compound according to claim 1 wherein $R^2$ and $R^3$ are independently hydrogen or $C_{1-4}$alkyl.

4. A compound according to claim 1 wherein one of $R^2$ and $R^3$ is hydrogen or methyl and the other is hydrogen.

5. A compound according to claim 1 which is:
6-[4-(1,4-dihydro-4-oxo-2-pyrimidinylamino)phenyl]-5-methyl-4,5-dihydro-3(2H)-pyridazinone or a pharmaceutically acceptable salt thereof.

6. A compound according to claim 1 which is:
6-[4-(1,4-dihydro-6-methyl-4-oxo-2-pyrimidinylamino)-phenyl]-5-methyl-4,5-dihydro-3(2H)-pyridazinone or a pharmaceutically acceptable salt thereof 7. A compound according to claim 1 which is:
6-[4-(1,4-dihydro-5-methyl-4-oxo-2-pyrimidinylamino)-phenyl]-5-methyl-4,5-dihydro-3(2H)-pyridazinone, or a pharmaceutically acceptable salt thereof.

8. A compound according to claim 1 which is:
6-[4-(1,4-dihydro-4-oxo-2-quinazolinylamino)phenyl]-5-methyl-4,5-dihydro-3(2H)-pyridazinone, or a pharmaceutically acceptable salt thereof.

9. The (R) isomer of a compound according to claim 2.

10. A compound according to claim 2 in which the (R) isomer is enantiomerically enriched.

11. A compound according to claim 1 which is (R) -6-[4-(1,4-dihydro-4-oxo-2-pyrimidinylamino)phenyl]-5-methyl-4,5-dihydro-3(2H)-pyridazinone or a pharmaceutically acceptable salt thereof.

12. A compound according to claim 1 which is (R) -6-[4-(1,4-dihydro-4-oxo-2-pyrimidinylamino)phenyl]-5-methyl-4,5-dihydro-3(2H)-pyridazinone or a pharmaceutically acceptable salt thereof substantially free of the (S) isomer.

13. A pharmaceutical composition for stimulating cardiac activity which comprises an effective amount of a compound according to claim 1 and a pharmaceutically acceptable carrier.

14. A pharmaceutical composition for stimulating cardiac activity which comprises an effective amount of a compound according to claim 5 and a pharmaceutically acceptable carrier.

15. A pharmaceutical composition for stimulating cardiac activity which comprises an effective amount of a compound according to claim 11 and a pharmaceutically acceptable carrier.

16. A method for stimulating cardiac activity in a mammal comprising internally administering an effective amount of a compound according to claim 1.

17. A method for stimulating cardiac activity in a mammal comprising internally administering an effective amount of a compound according to claim 5.

18. A method for stimulating cardiac activity in a mammal comprising internally administering an effective amount of a compound according to claim 11.

19. A method for effecting bronchodilatation in a mammal comprising internally administering an effective amount of a compound according to claim 1.

20. A method for effecting bronchodilatation in a mammal comprising internally administering an effective amount of a compound according to claim 5.

21. A method for effecting bronchodilatation in a mammal comprising internally administering an effective amount of a compound according to claim 11.

* * * * *